(12) United States Patent
Tompkins et al.

(10) Patent No.: US 12,121,734 B2
(45) Date of Patent: Oct. 22, 2024

(54) BIOCOMPATIBLE HOUSING

(71) Applicant: Wyss Center for Bio and Neuro Engineering, Genèva (CH)

(72) Inventors: Dana D. Tompkins, Frederick, CO (US); Christopher D. Gongora, Lyons, CO (US); Achim Kitschmann, Basel (CH); Jennifer Losasso-Tompkins, Frederick, CO (US); Claude Clément, Geneva (CH)

(73) Assignee: WYSS CENTER FOR BIO AND NEURO ENGINEERING, Geneva (CH)

( * ) Notice: Subject to any disclaimer, the term of this patent is extended or adjusted under 35 U.S.C. 154(b) by 305 days.

(21) Appl. No.: 17/503,882

(22) Filed: Oct. 18, 2021

(65) Prior Publication Data

US 2022/0105349 A1 Apr. 7, 2022

Related U.S. Application Data

(62) Division of application No. 16/669,163, filed on Oct. 30, 2019, now Pat. No. 11,147,978.

(51) Int. Cl.
*A61N 1/375* (2006.01)
(52) U.S. Cl.
CPC .................. *A61N 1/3754* (2013.01)
(58) Field of Classification Search
CPC .......................... A61N 1/3754; A61N 1/3605
See application file for complete search history.

(56) References Cited

U.S. PATENT DOCUMENTS

| | | | |
|---|---|---|---|
| 4,516,820 | A | 5/1985 | Kuzma |
| 5,455,456 | A | 10/1995 | Newman |

(Continued)

FOREIGN PATENT DOCUMENTS

| | | |
|---|---|---|
| CN | 102481449 A | 5/2012 |
| CN | 109999343 A | 7/2019 |

(Continued)

OTHER PUBLICATIONS

PCT International Preliminary Report on Patentability and Written Opinion for International Application No. PCT/IB2020/059532, entitled Feedthrough Protective Cover; Mailed on May 12, 2022.

(Continued)

*Primary Examiner* — Amanda K Hulbert
*Assistant Examiner* — Philip C Edwards
(74) *Attorney, Agent, or Firm* — Hamilton, Brook, Smith & Reynolds, P.C.

(57) ABSTRACT

Implantable medical devices have a feedthrough from the device to the outside world to pass electrical current from electronics inside the implant to the patient or vice versa. A plurality of sensors and/or signal wires in a wire bundle must connect to the feedthrough and implant in living tissue in the patient. Chemical and physical forces work against the wire connections on the feedthrough. Disclosed embodiments include a biocompatible housing that can be used for an implantable medical device. The biocompatible housing includes a recess with at least one wire exit port, the recess having at least one feedthrough assembly mounted therein. A wire of the feedthrough assembly passes out the wire exit port, and the recess has a top hermetically sealed over it.

10 Claims, 14 Drawing Sheets

(56) References Cited

U.S. PATENT DOCUMENTS

| | | | |
|---|---|---|---|
| 6,052,623 A | 4/2000 | Fenner et al. | |
| 6,519,133 B1 | 2/2003 | Eck et al. | |
| 6,597,953 B2 | 7/2003 | Boling | |
| 6,622,046 B2 | 9/2003 | Fraley et al. | |
| 8,224,434 B2 | 7/2012 | Greene | |
| 8,267,708 B1 * | 9/2012 | Sochor | H01R 24/58 439/289 |
| 8,396,557 B2 | 3/2013 | DiLorenzo | |
| 8,532,783 B2 | 9/2013 | Zimmerling et al. | |
| 8,538,530 B1 * | 9/2013 | Orinski | A61N 1/3754 607/36 |
| 8,862,235 B1 | 10/2014 | Stover et al. | |
| 10,433,754 B2 | 10/2019 | Nurmikko et al. | |
| 10,568,574 B2 | 2/2020 | Williams et al. | |
| 11,147,978 B2 | 10/2021 | Tompkins et al. | |
| 2002/0138114 A1 | 9/2002 | Gramse | |
| 2003/0109903 A1 | 6/2003 | Berrang et al. | |
| 2005/0283203 A1 | 12/2005 | Flaherty et al. | |
| 2006/0173259 A1 | 8/2006 | Flaherty et al. | |
| 2012/0012374 A1 | 1/2012 | Koester et al. | |
| 2012/0168884 A1 | 7/2012 | Yao et al. | |
| 2012/0302856 A1 | 11/2012 | Chang et al. | |
| 2015/0157862 A1 | 6/2015 | Greenberg et al. | |
| 2016/0278899 A1 | 9/2016 | Heller et al. | |
| 2017/0237199 A1 | 8/2017 | Schüttler et al. | |
| 2017/0290521 A1 | 10/2017 | Angle et al. | |
| 2017/0319092 A1 | 11/2017 | Wendel-Mitoraj et al. | |
| 2018/0153474 A1 | 6/2018 | Aeschlimann et al. | |
| 2019/0246929 A1 | 8/2019 | Angle et al. | |
| 2020/0187861 A1 | 6/2020 | Williams et al. | |
| 2020/0330749 A1 | 10/2020 | Gribetz et al. | |
| 2021/0128927 A1 | 5/2021 | Tompkins et al. | |

FOREIGN PATENT DOCUMENTS

| | | |
|---|---|---|
| EP | 1614443 A1 | 1/2006 |
| GB | 2134 335 A | 8/1984 |
| JP | 2006-263469 A | 10/2006 |
| JP | 2017-136331 A | 8/2017 |
| WO | 9706853 A1 | 2/1997 |
| WO | 99/31933 A1 | 6/1999 |
| WO | 2021084351 A1 | 5/2021 |

OTHER PUBLICATIONS

Bjune, C., "Advancement in Microelectronics Packaging for Medical Implants: Solving the Need for "More" with "Less" Space," Draper, 55 pages (May 7, 2019).

PCT International Search Report and Written Opinion for International Application No. PCT/IB2020/059532, entitled "Feedthrough Protective Cover," mailed on Mar. 22, 2021.

U.S. Non-Final Office Action for U.S. Appl. No. 16/669,163, entitled "Feedthrough Protective Cover," mailed on Apr. 14, 2021.

U.S. Notice of Allowance for U.S. Appl. No. 16/669,163, entitled "Feedthrough Protective Cover," mailed on Aug. 9, 2021.

* cited by examiner

BIOCOMPATIBLE HOUSING

RELATED APPLICATION(S)

This application is a divisional of U.S. application Ser. No. 16/669,163, filed Oct. 30, 2019. The entire teachings of the above application is incorporated herein by reference.

BACKGROUND

Implantable medical devices are often sealed, in whole or in part, to protect against the ingress of substances from the implant environment, e.g., fluids inside the human body. Sealing, e.g., hermetic sealing, can be achieved by surrounding the device, or desired portions thereof, with one or more sealing elements that define and enclose a region of the device ("sealed region") that is suitably segregated from the implant environment. The sealed elements can be formed or joined together so that the joints or connections among them are tight, and the sealing elements comprise a "seal" around the sealed region.

The sealing elements can be comprised of a variety of materials, selected for their desired material, chemical, and physical properties. In many applications, sealing elements are chosen to be impervious, or substantially impermeable, to liquids and/or gases. Desirably, they also do not corrode or react with chemical or biological materials in the implant environment, they are biocompatible, and they do not trigger adverse biological reactions in the implant host.

Many implantable medical devices require the transmission of electrical impulses across the seal. To achieve this, a special sealing element called a "feedthrough device" can be integrated into the seal. Feedthrough devices are typically designed to allow one or more channels of electrical conduction across their width being impervious to the flow of liquids and/or gases. These conductive channels (e.g., conductive pins or vias) can be embedded, for example, in a material such as a ceramic disk that is electrically insulating and that forms a central region of the feedthrough device.

On the internal surface of the feedthrough device, the conductive channels are typically connected to the internal circuity of the medical device; and on the external surface of the feedthrough device, they are connected, for example, to wires or electrodes. One example of a feedthrough device is provided in U.S. Pat. No. 6,052,623 (2000) to Fenner et al., relevant sections of which are herein incorporated by reference. As shown in FIGS. 2 and 3 of Fenner, the external tip of a conductive pin protrudes from an insulator on the outside of the medical device case.

Some feedthrough devices can comprise hundreds of (e.g., 500) conductive paths (pins or vias) located in a 0.1 to 10 $cm^2$ area, e.g., a 1 $cm^2$ of the feedthrough (e.g., in the ceramic disk region). If lead wires (for example, similar to those noted in the '623 patent above) are attached (e.g., robotically welded) to the conductors (e.g., pins), then the lead wire density is accordingly high.

A challenge with implantable medical devices is forming a secure and durable connection (e.g., by welding) between the external conductive element of a feedthrough device (e.g., pin) and the next element in the external conductive path (e.g., a lead wire). When the device is surgically implanted in the (human) body, it is subject to physical stresses as well as chemical reactions that can break the connections/welds or cause fracture in the wires themselves.

What is needed in the art are methods and devices for protecting from chemical and physical stresses the electrical connections and wires at the external surfaces of feedthrough devices.

SUMMARY

In some aspects, the present invention relates to protecting from mechanical and chemical forces feedthrough wires and connections in an implantable medical device.

The present invention also relates, in some aspects, to improved methods and apparatus for protecting high density feedthroughs through a combination of a protective cap and a backfill material. These two components have been discovered to work synergistically to provide advantages not found in the prior art.

For example, there can be selected a combination of a first set of mechanical and material properties found in the cap (e.g., strength and rigidity to protect against gross material deformation on impact) with a second set of mechanical and material properties found in the backfill (e.g., sufficient flexibility to envelop and protect the fine wires of the feedthrough against transmission of shock from the cap). In this manner, the degree of protection is markedly enhanced. Further, use of the backfill in this manner provides the additional advantage of filling the void space under the cap, thereby limiting or preventing the ingress of biological fluids or tissues.

In some embodiments, a protective cap is placed over some or all of the feedthrough device and around the external wires, which are optionally formed into a wire bundle. The cap has an opening (wire port) to allow passage therethrough of the wires/wire bundle. The protective cap prevents forces from outside the implanted device from being transmitted directly to delicate substrate regions of the feedthrough device (e.g., ceramic substrate), regions with conductive pins or vias, or regions of the wires or welds of feedthroughs. In some embodiments, the protective cap is provided for feedthroughs without protruding pins or with minimally protruding feedthrough pins (e.g., less than 1 mm).

In some embodiments, the cap is comprised of a surface that is approximately parallel (e.g., up to 15 degrees from parallel) to the feedthrough substrate.

In some embodiments, the cap has wall portions that space the parallel surface from the plane of the feedthrough substrate surface by a distance ranging from about 25 micrometers to about 25 millimeters.

The protective cap can either be integral to a housing, or welded or bonded onto the housing of an Implantable Medical Device.

In some embodiments, the protection cap is used with feedthroughs having fewer than 500 pins.

The protective cap can be formed from a wide variety of materials, including without limitation, metals (e.g., titanium), polymers, ceramics, or other biocompatible metals or materials.

In some embodiments, the space between the protective cap and the feedthrough substrate is filled with a biocompatible material, such as an insulating polymer such as silicone, epoxy, polyurethane, or other insulating polymer or sealant that flows and insulates the region.

The biocompatible material can provide further mechanical protection against shock, stress and fracture as well as further protecting against exposure of the wires and welds to biological fluids in the implant environment.

In some embodiments, the biocompatible filling material rigidly, e.g., in the case of epoxy, encapsulate the wires and wire bonds.

In some embodiments, the biocompatible filling material elastically, e.g., in the case of silicone or other viscoelastic polymer, encapsulates the wires and wire bonds.

In some embodiments, more than one filling material is used, e.g., using both rigid and flexible polymers to encapsulate the wires and wire bonds.

In some embodiments, the protective cap is formed of a rigid material and the biocompatible filling material is formed of a more elastic material.

Another aspect of the present invention relates to providing a housing with a recess for (cap protected) feedthroughs, and in some embodiments to also providing optional tops and/or sealants for the recess.

The invention also includes a stand-alone cap formed of a biocompatible material with a protection plane essentially parallel to the ceramic plane of the feedthrough that is welded or otherwise bonded to the feedthrough.

Other aspects of this invention will appear from the following description and appended claims, reference being made to the accompanying drawings forming a part of this specification wherein like reference characters designate corresponding parts in the several views.

Figure 1:
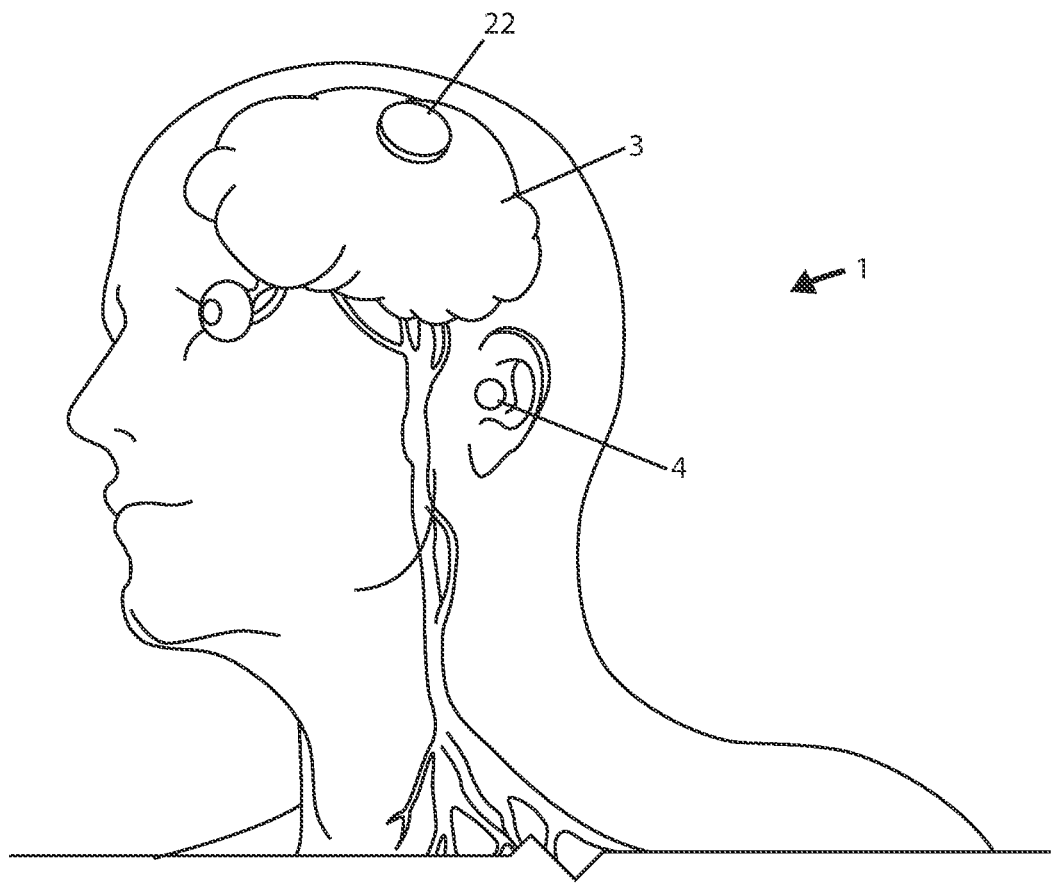
FIG. 1 (prior art) is an illustration of an implanted medical device on the skull.

Before explaining the disclosed embodiments in detail, it is to be understood that the embodiments are not limited in application to the details of the particular arrangements shown, since other embodiments are possible. Also, the terminology used herein is for the purpose of description and not of limitation. The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

Referring first to FIG. 1 (prior art) the patient 1, shown with brain 3, may have a medical implant 22 in, under, or above the skull to control prostheses by registering brain waves. Other implants are also possible in, under, or above other parts of the body. For example, a hearing medical implant 4 converts sound into electrical impulses. Implants can generally be for anything that must transmit or receive many channels of electrical signals. These implants 2, 4 must survive the chemical and physical environment into which they are implanted (e.g., human body), which includes physical stresses from impact, growth of the host organism, and personal grooming and activities, e.g., haircuts.

Figure 2:
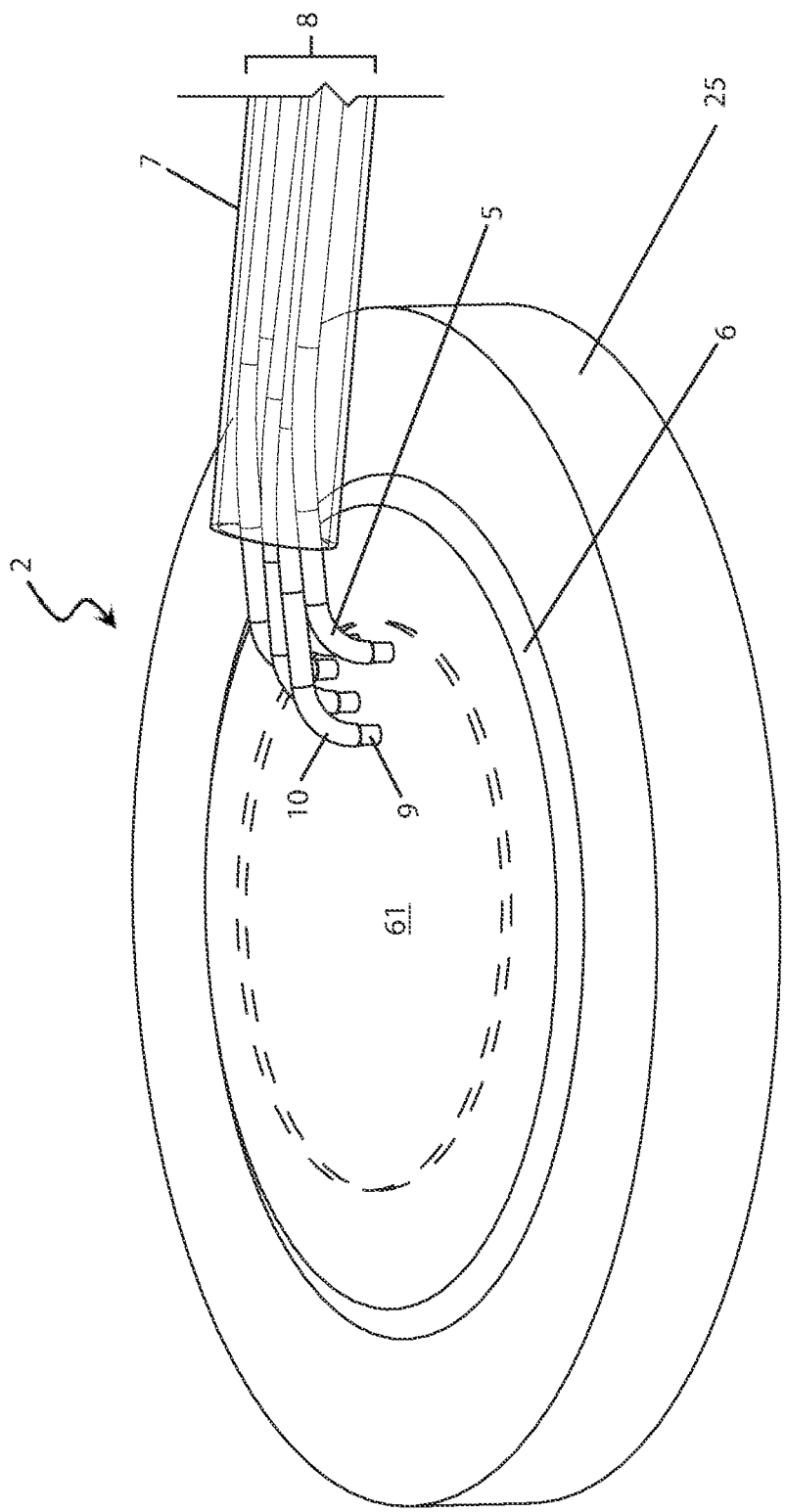
FIG. 2 is a top perspective view of an implantable medical device feedthrough device with sensor wires robotically welded to it and a sheath around wires.

Referring next to FIG. 2 the medical implant feedthrough device 2 has a plurality of wires 5 (nominally 1/1000 inch diameter) that are robot welded to a top surface of the electrically conductive vias or pins of a feedthrough disc 6 (e.g., a ceramic insulator). The dashed lines 61 on disc 6 represent the outer diameter of the vias area. A weld flange 25 is shown surrounding the feedthrough disk 6. A sheath 7 can cover the bundle of wires, the bundle can be held together with a polymer, or the bundle can have free floating wires designated 8. A sheath is defined herein to include a physical encapsulation of metallic wires in a polymer by any means.

Each wire 5 has an exposed metal tip 9 used in the weld operation. Each wire 5 has an insulator 10 covering the conductive filament of which metal tip 9 is made.

Figure 3:
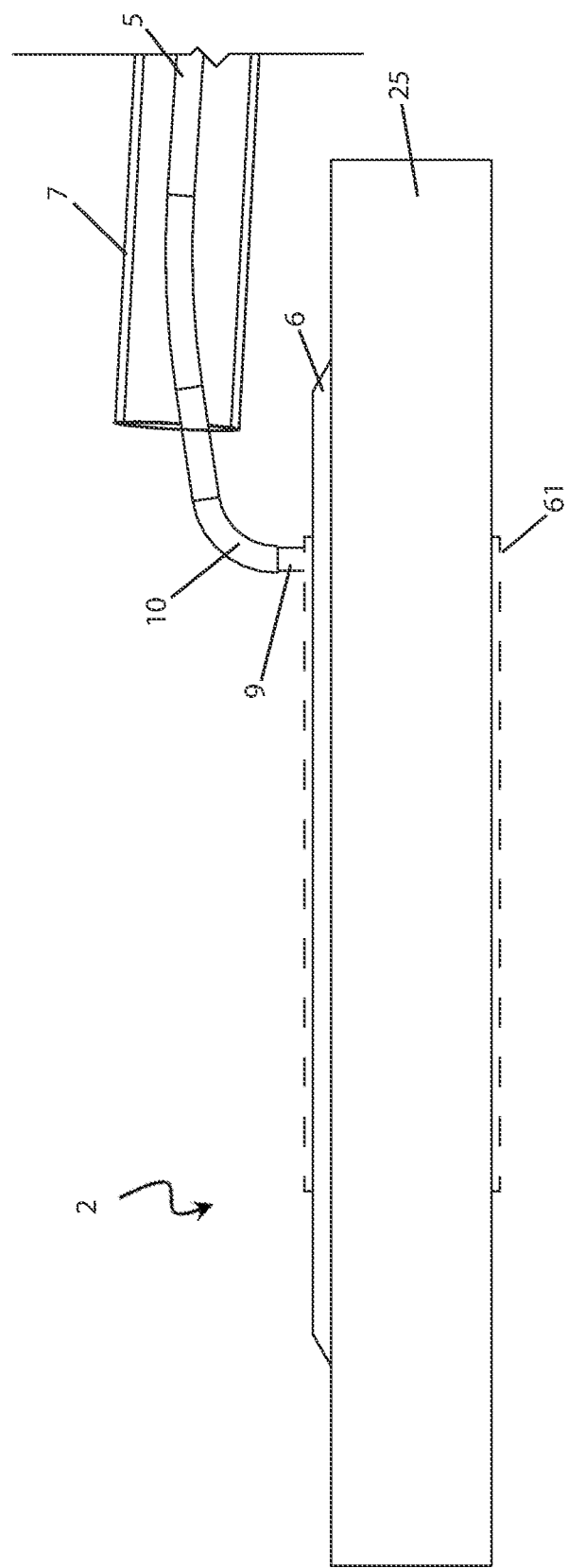
FIG. 3 is a side elevation view of one wire from the FIG. 2 embodiment.

Referring next to FIG. 3 each metal tip 9 is welded to a via or pin of the feedthrough device. Where, as here, reference is made to welding, or to welded materials, it should be appreciated that a wide variety of alternate assembly techniques may be used instead. These techniques include, for example, wire bonding, brazing, soldering, or the use of metallic or nonmetallic adhesives (e.g., polymeric adhesives) as in gluing. In addition, welding should be appreciated to encompass a variety of techniques, including both "hot" techniques, which involve the application of heat (e.g., arc welding, friction welding, ultrasonic welding, and laser welding) and "cold" techniques, which do not involve an appreciable application of heat and instead rely primarily on the application of pressure to join materials (i.e., cold pressure welding or contact welding).

Figure 4:
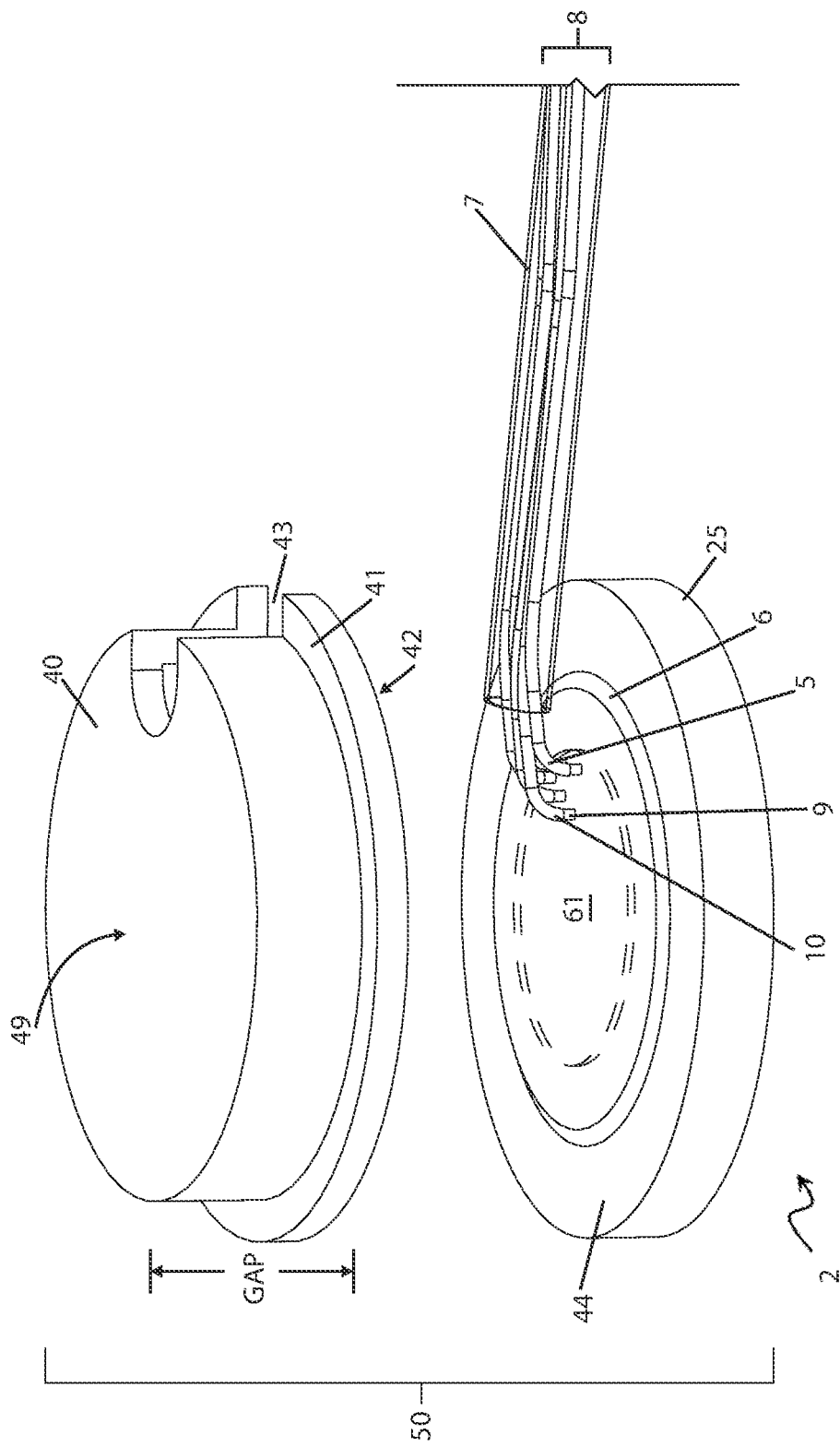
FIG. 4 is an exploded view of a combination of the FIG. 2 embodiment and a protective top.

Referring next to FIG. 4 a protective top (cap) 40 has a bundle exit port 43 and a mounting ridge 41 with a mounting surface 42. The mounting surface 42 mounts atop receiving surface 44. The top can be made from a wide variety of materials, including metals such as titanium and platinum; metal alloys such as chromium cobalt alloys, nickel-cobalt based alloys (e.g., MP35N), stainless steel (SS); polymers such as polyether ether ketone (PEEK) and polyetherimide (ULTEM); ceramics; fiber-reinforced plastic; and materials such as sapphire and glass.

The indicated GAP represents the spacing between the interior aspect of upper surface 49 and the exterior lower aspect of mounting surface 42. This spacing can range, for example, from about 0.25 mm to about 25 mm. In some embodiments, such as when the upper surface is flat and parallel to the plane of the mounting surface, the GAP spacing will be constant across the area of the protective top. In other embodiments, the GAP spacing will not be constant. In such as case, e.g., when the upper surface of the protective top is convex, the maximum GAP spacing can be used as a measure of the upward projection of the protective cap.

Top 40 can be combined with feedthrough device 2 in a variety of ways, such as via the following procedure: forming a top having a thickness ranging from about 0.2 mm to about 2.0 mm; forming a gap under the top ranging from about 0.25 mm to about 25 mm; forming a mounting ridge on the top to match a shape and size of a receiving surface base on the feedthrough device; cleaning the receiving surface 44 and the mounting ridge 42 with a solvent and/or air or plasma; connecting a bundle of feedthrough wires to a plurality of feedthrough pads; welding or gluing the mounting ridge to the receiving surface base; passing the wire bundle through an exit port of the top; injecting sealant(s) into the exit port to "pot" the wire bundle; and adding a high-level moisture protection coating (e.g., multilayer coatings with alternating organic and non-organic materials; or coating with atomic layer deposition) before and/or after potting with sealants or polymers. Several layers of different materials can be used for the potting.

The potting and/or sealing materials can be potted into all or a portion (e.g., greater than about 25%, 50%, 75%, or 90% of the cavity (e.g., as a percentage of either cavity volume, or of linear distance along the axis of maximum GAP spacing) formed between the protective cap and the feedthrough device. In some embodiments, the materials will completely occlude the opening(s) to the protective top through which the wires pass so as to prevent ingress of biological fluids into all or a substantial portion (e.g., >75%, 90%, 95%) of the volume under the protective top. In some embodiments, the potting material flows around the assembled wires so that the post-potting void (or gas) volume is less than about 5%, 1%, 0.1% of the total potted volume. Analogous volume and coverage considerations apply to the filling of the device cavities described herein, including those in which protective tops are not used.

Figure 5:
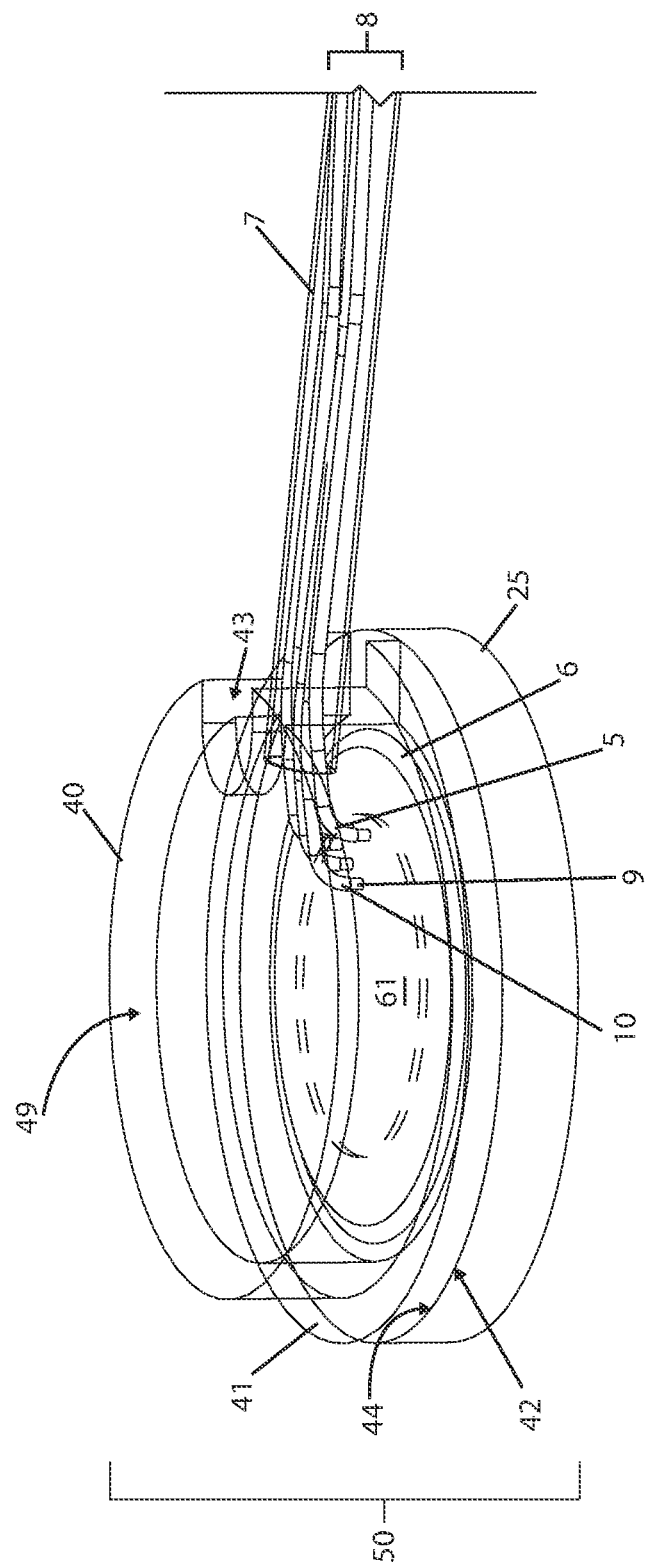
FIG. 5 is a top perspective view of the FIG. 4 embodiment assembled to form a composite assembly.

Referring next to FIG. 5 the top 40 is installed on the feedthrough device 2 to form composite assembly 50. Top 40 has a flat upper surface 49. However, top 40 can assume a wide variety of shapes, referred to generally herein as "domes," which is intended to cover all shapes and sizes of protective top that projects upward from the feedthrough substrate, including without limitation those with flat, concave, and convex upper surfaces. As used herein, the term "dome" can include any structure covering an underlying object.

Figure 6:
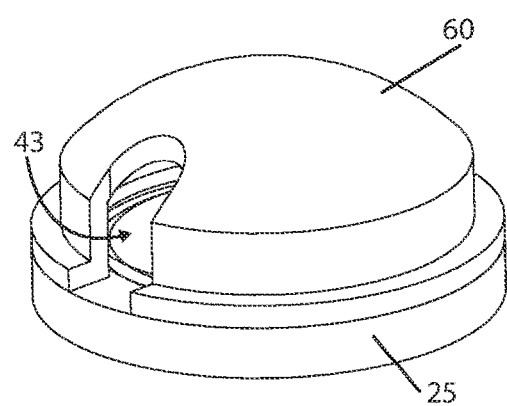
FIG. 6 is a top perspective view of a protective top having a convex upper surface, together with the feedthrough device, forming a composite assembly.

FIG. 6 shows a composite assembly including top 60, which is a dome with a convex upper surface.

Figure 7:
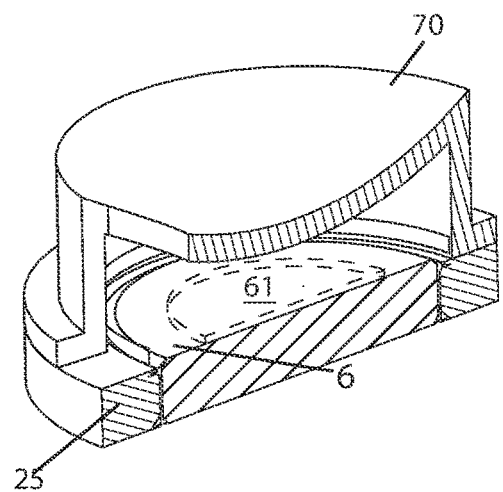
FIG. 7 is a sectional view of a protective top having a concave upper surface, together with the feedthrough device, forming a composite assembly.

FIG. 7 shows a composite assembly including top 70, which is a dome with a concave upper surface.

Figure 8:
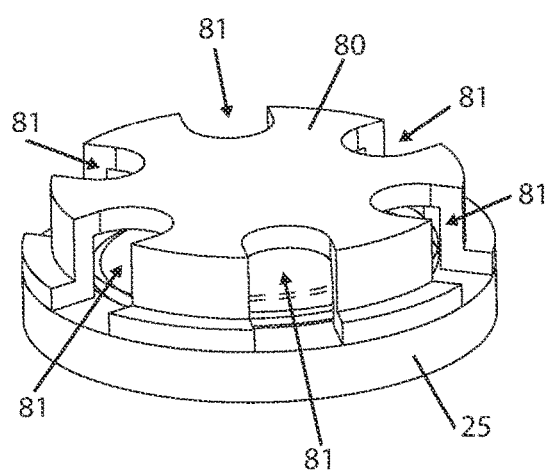
FIG. 8 is a top perspective view of a protective top having a flat, multi-exit top, together with the feedthrough device, forming a composite assembly.

FIG. 8 shows a composite assembly including top 80, which is a dome with a flat upper surface with multiple wire exit ports 81.

Figure 9:
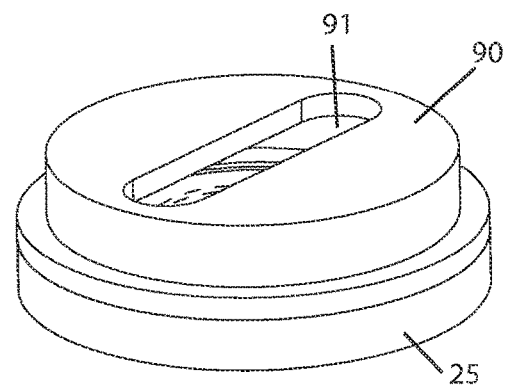
FIG. 9 is a top perspective view of a protective top having a flat, slotted top, together with the feedthrough device, forming a composite assembly.

FIG. 9 shows a composite assembly including top 90, which is a dome with a slot 91 on its top surface serving as an exit port.

Figure 10:
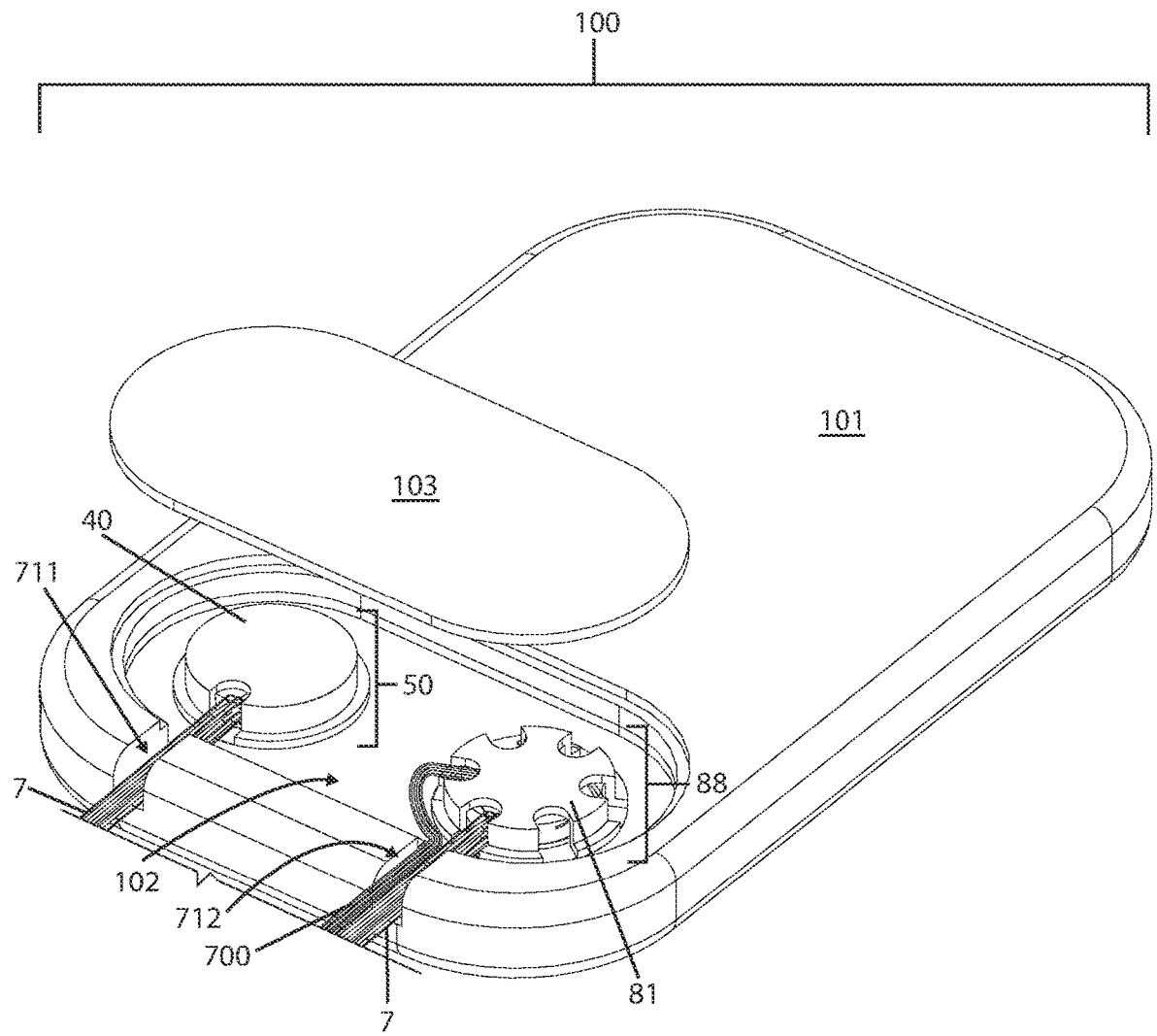
FIG. 10 is a top perspective view of an implantable medical device with a recess for two composite assemblies, each assembly having a feedthrough device and a protective top, the recess being sealable with a lid.

Referring next to FIG. 10 an implantable medical device 101 has a composite assembly 50 and a composite assembly 88 seated in a recess 102 which can be sealed with a cover 103. The assembly is designated 100. The second wire bundle 700 can share the housing exit port 712 which can be the same size as housing exit port 711. Any of these composite assemblies (50, 88) can have a wide variety of widths, for example from about 3 mm to about 40 mm; and they can be of any shape including round, oblong, rectangular with rounded edges, and so on. The wires (uninsulated) can have a wide range of widths, for example from about 0.01 mm to about 0.1 mm. One or more sealants can be injected into recess 102. Sealants can include, without limitation epoxy, polyurethane, and silicone. The housing exit ports 711, 712 can be used to inject the sealant(s).

Figure 11:
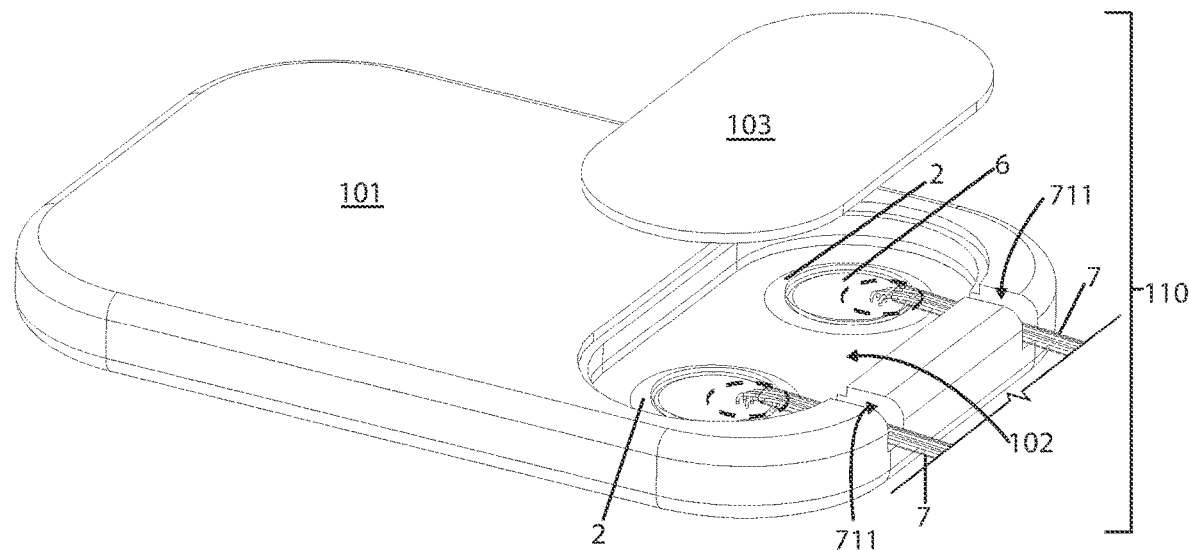
FIG. 11 is a top perspective view of an implantable medical device with two feedthrough devices not having tops, housed in a recess with a lid.

Referring next to FIG. 11 the assembly 110 comprises an implantable medical device 101 with a recess 102 and two non-capped feedthrough assemblies 2 as shown in FIG. 2. No sealant is shown in this embodiment.

Figure 12:
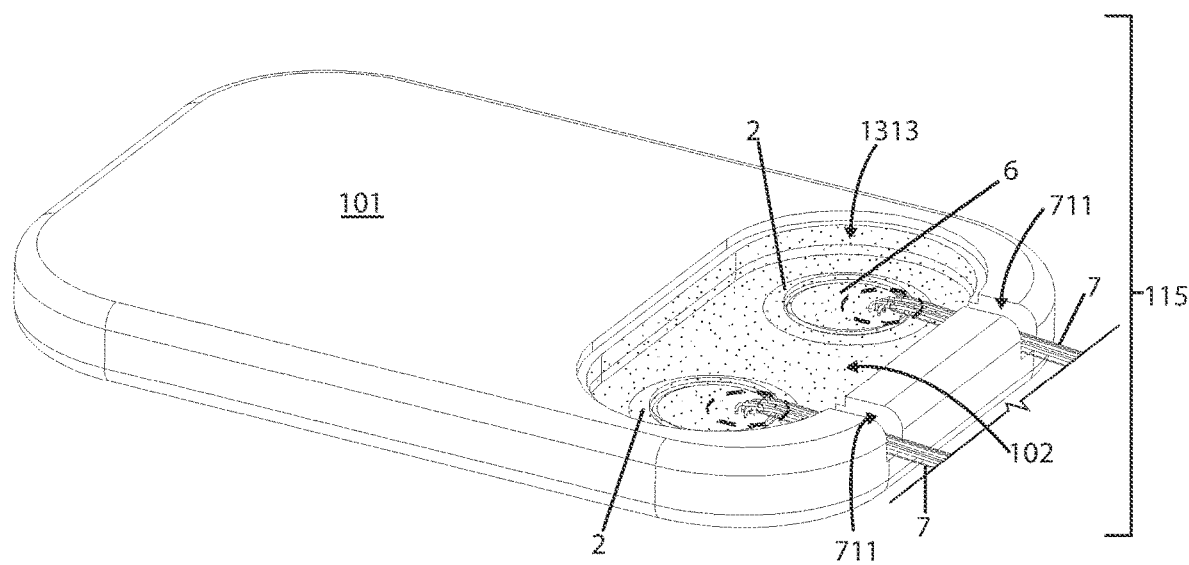
FIG. 12 is the same view as FIG. 11 without the lid and showing filling with a sealant as shown in FIG. 16.

Referring next to FIG. 12 the assembly 115 comprises an implantable medical device 101 with a recess 102. A thick sealant 1313 as shown in FIG. 16 is shown.

Figure 13:
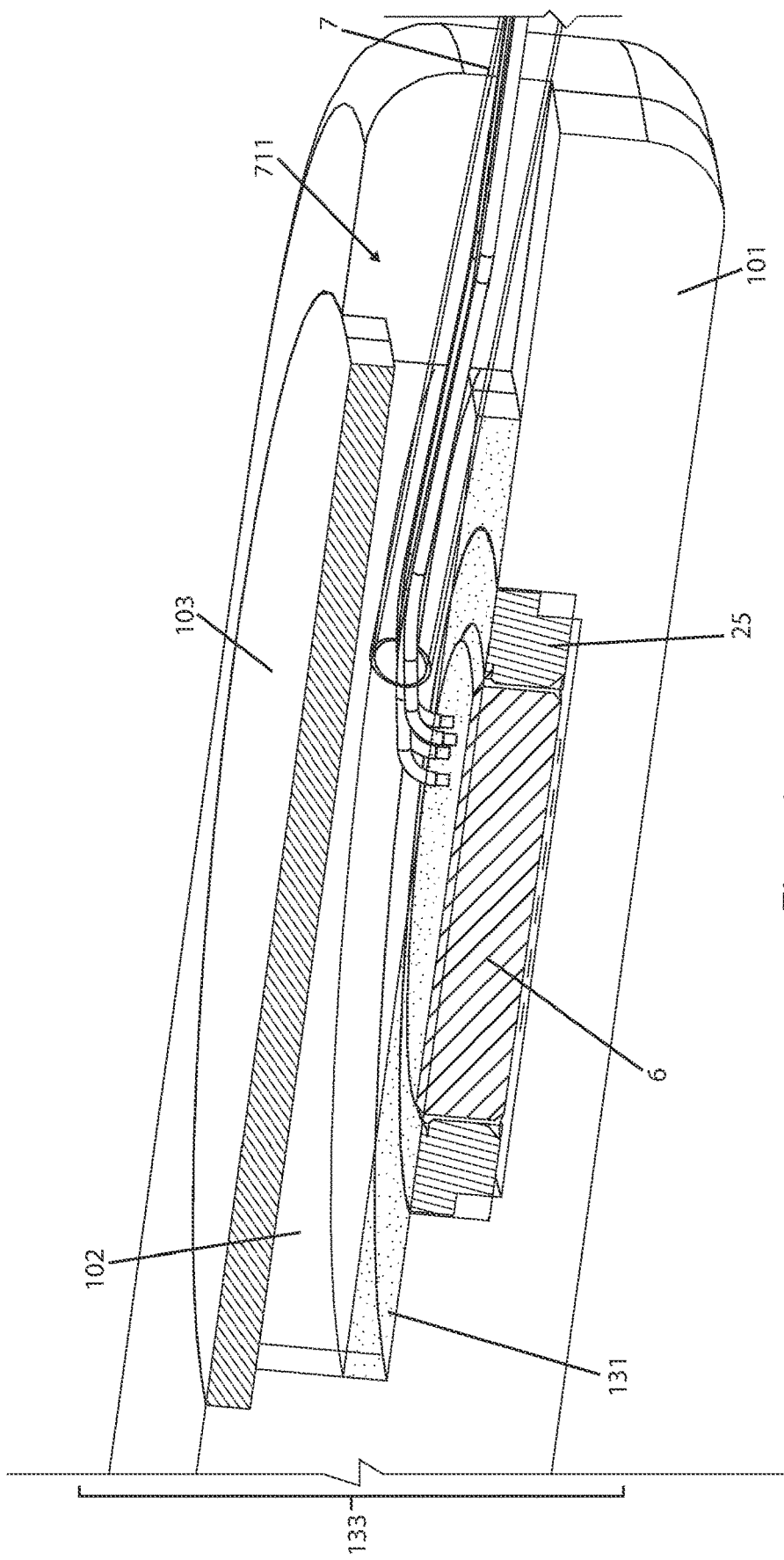
FIG. 13 is a sectional view of one feedthrough in the FIG. 11 embodiment and having a lower sealant as shown in FIG. 14.

Referring next to FIG. 13 the assembly 133 comprises a non-cap feedthrough 2 with its wire bundle 7 exiting the housing exit port 711. A (high durometer) sealant 131 is used as shown in FIG. 14.

Figure 14:
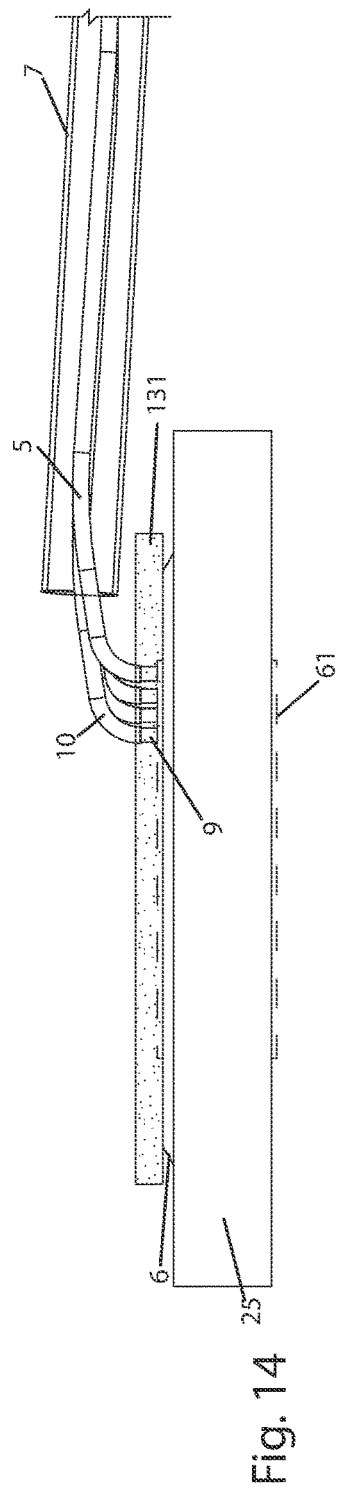
FIG. 14 is a side elevation view of an implantable medical device feedthrough device with a lower sealant.
Figure 15:
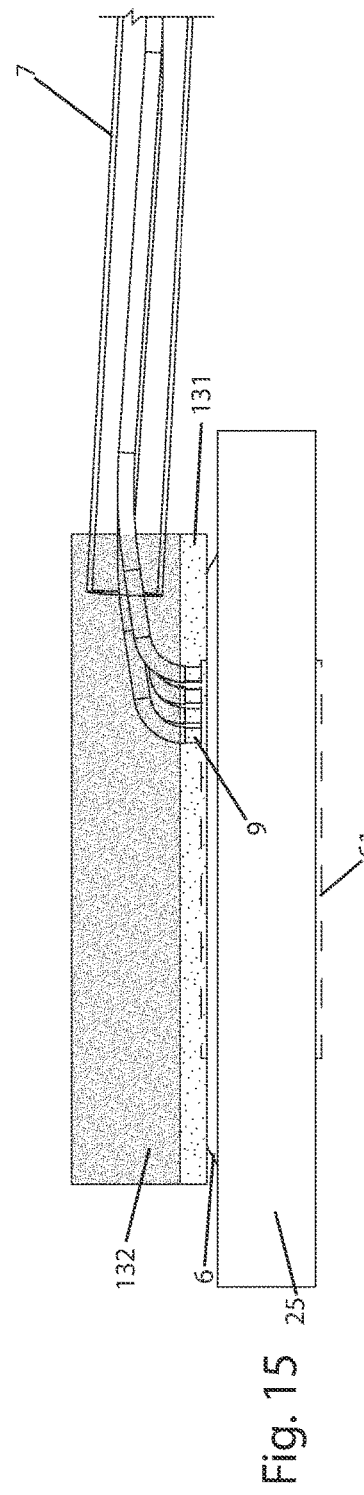
FIG. 15 is a side elevation view of an implantable medical device feedthrough device with a lower and an upper sealant.

Referring next to FIG. 14 the feedthrough 2 has had a sealant 131 injected to cover the wire tips 9. This sealant 131 can be a high durometer polymer such as an epoxy or silicone to protect the weld on metal tip 9. In FIG. 15 a (softer) sealant 132 has been added atop sealant 131 to allow strain relief and mechanical impedance transition between the more rigid encapsulant and the external environment for the wire bundle 7.

Figure 16:
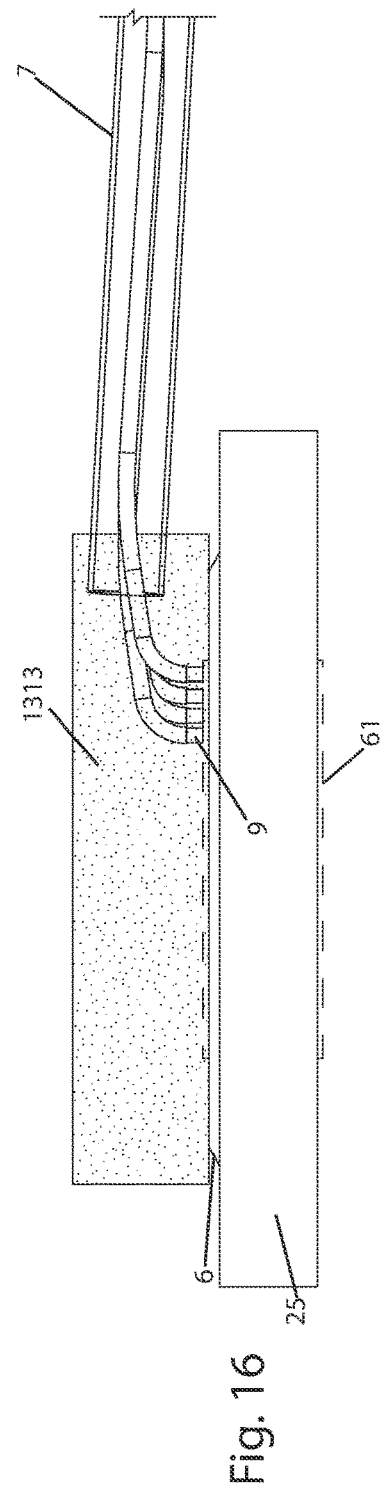
FIG. 16 is a side perspective view of an implantable medical device feedthrough device with one thick sealant.

In FIG. 16 a single thick sealant 1313 is shown.

Figure 17:
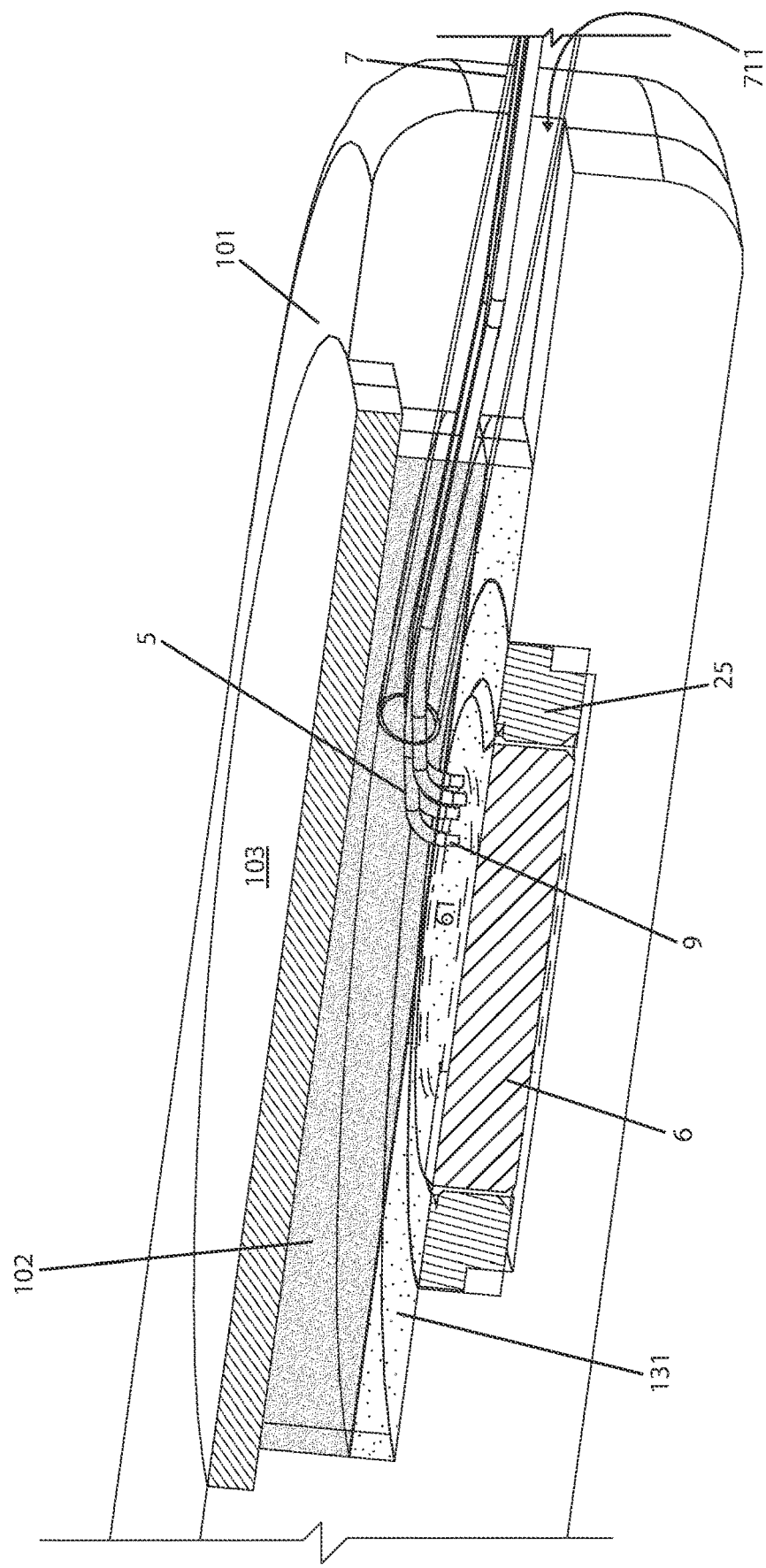
FIG. 17 is a sectional view of an implantable medical device in a housing with a recess having a dual (upper and lower) sealant as shown in FIG. 15, and a lid.

Referring next to FIG. 17 an implantable medical device 101 has a recess 102 with a feedthrough device 2. A sealant 131 (see FIG. 14) covers the bottom of the recess 102. A lid (or top) 103 seals the recess 102.

Figure 18:
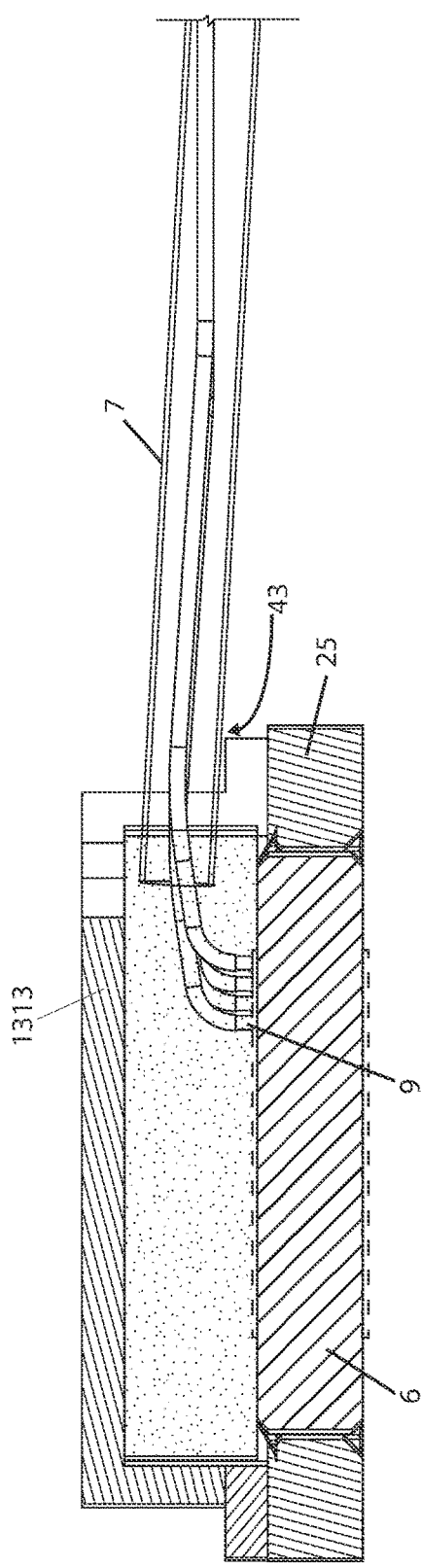
FIG. 18 is a sectional view of an implantable medical device feedthrough device with one thick sealant as shown in FIG. 16 and a protective top.

Referring next to FIG. 18 the feedthrough device 2 has a cap 40, and a sealant 1313 seals the space under the dome of the cap 40. See FIGS. 4 and 16.

Figure 19:
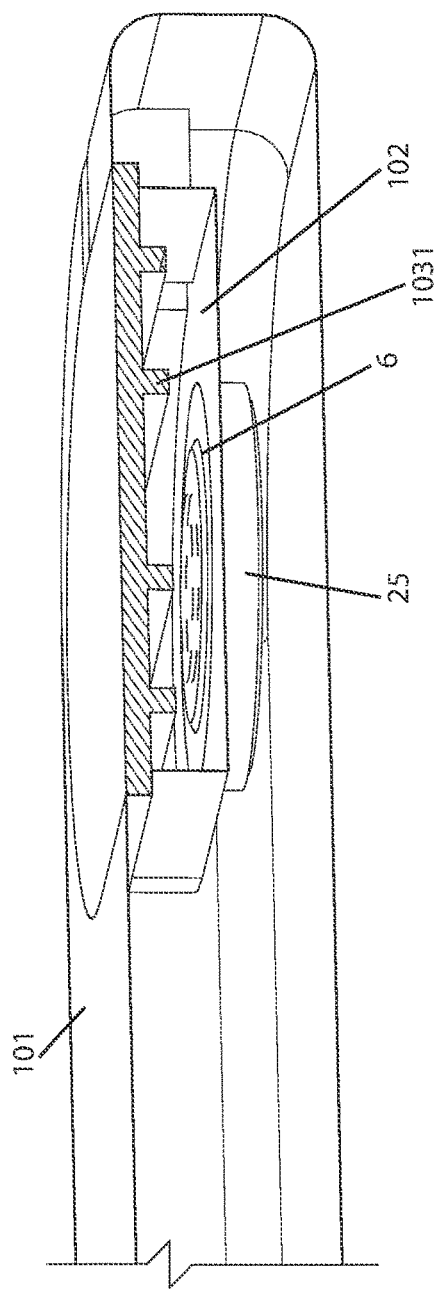
FIG. 19 is a sectional view of an implantable medical device in a housing with a recess having a ribbed top for strengthening.

Referring next to FIG. 19 the implantable medical device 101 has a recess 102 with a top 1030. The top 1030 has reinforcement ribs 1031.

Figure 20:
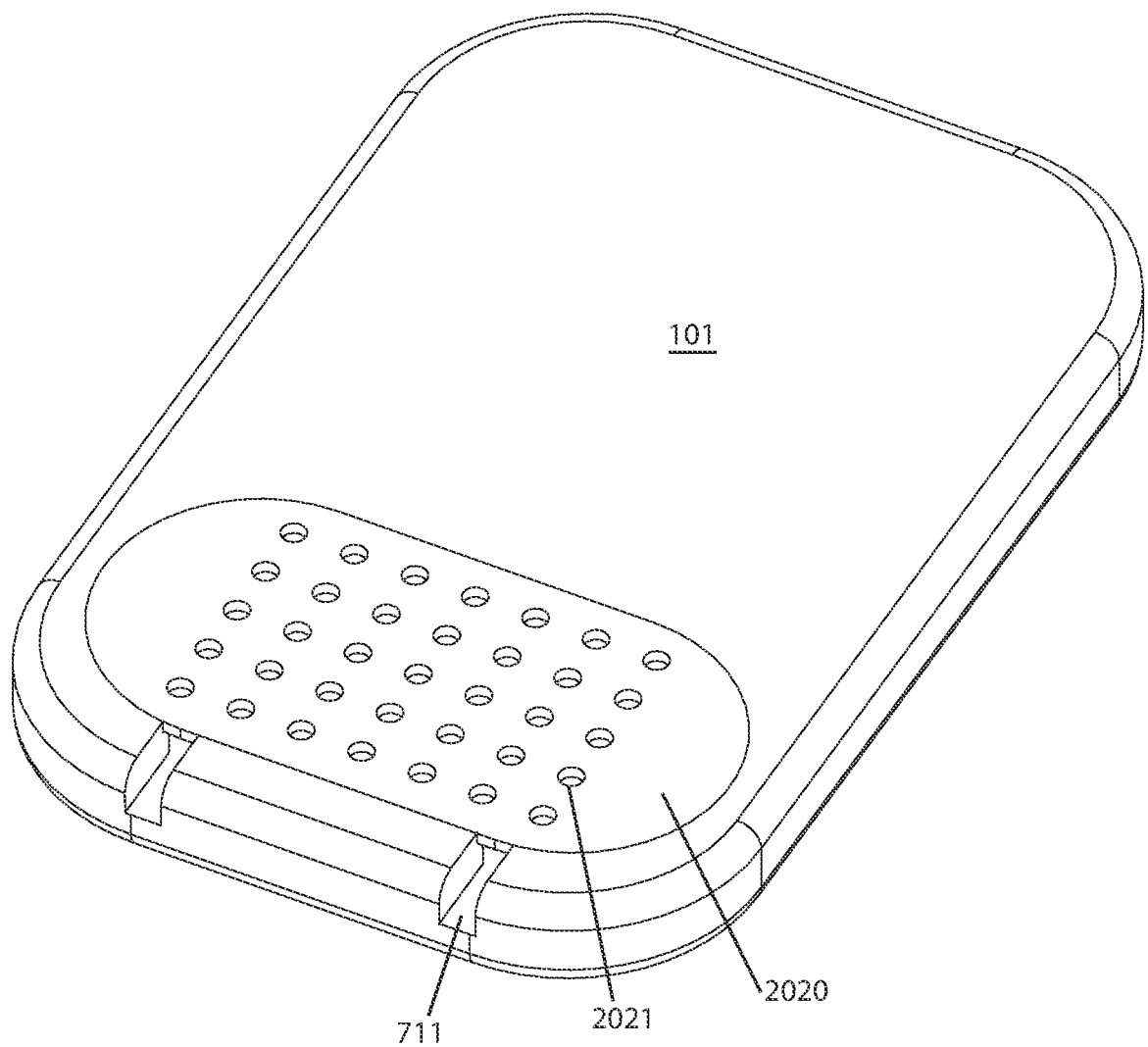
FIG. 20 is a top perspective view of a housing with a top having fill or vent holes.

Referring next to FIG. 20 the top 2020 has holes 2021 which can be used as vents or fill holes.

Figure 21:
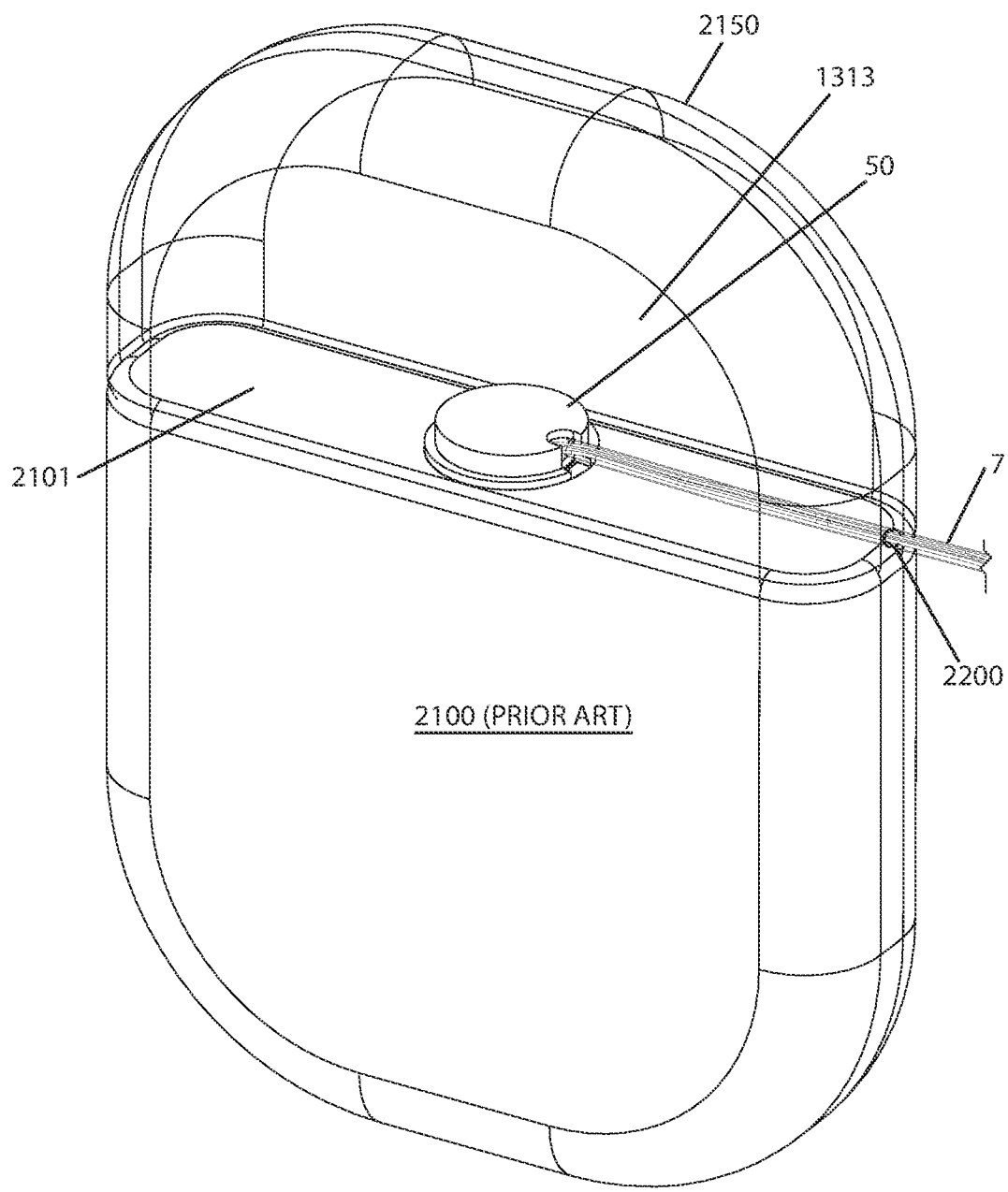
FIG. 21 is a side perspective view of a housing for an implantable medical device with a feedthrough under a sealant header.

Referring next to FIG. 21 a (prior art) implantable medical device 2100 has a mounting surface 2101 upon which a composite assembly 50 (see FIG. 4) is mounted. A sealant header 2150 is sealed over the mounting surface 2101. The wire bundle 7 passes out an exit port 2200. A sealant 1313 fills the sealant header 2150.

As used herein, the term "a plurality of wires, a bundle of wires and an associated wire exit port" includes a bundle of wires, all sorts of cables, including twisted, braided, coiled, coaxial, flat ribbons (polyimide, liquid crystal polymer), and metal strips.

In another aspect of the present invention, the feedthrough device and/or protective cap can comprise an independent sub-assembly of a larger device, the sub-assembly being created separately from, and prior to integration into, the larger device.

While a number of exemplifying features and embodiments have been discussed above, those of skill in the art will recognize certain modifications, permutations, additions and subcombinations thereof. No limitation with respect to the specific embodiments disclosed herein is intended or should be inferred.

The present invention is also applicable for a wide variety of implantable non-medical devices including RFID tags, communication implants, as well as non-implantable devices including wearables and sensors.

Relevant portions of the teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A biocompatible housing for an implantable medical device, the biocompatible housing comprising:
   a recess with at least one wire exit port;
   said recess having at least one feedthrough assembly mounted therein, a protective cap being mounted to the at least one feedthrough assembly, the protective cap having a top and a bottom, a gap being under the top, and a mounting ridge surrounding a perimeter of the gap, the mounting ridge having a bottom mounting surface sealed to a receiving surface base on the at least one feedthrough assembly, the mounting ridge matching a shape and size of the receiving surface base;
   wherein a wire of the feedthrough assembly passes out the wire exit port; and
   said recess further comprises a top cover hermetically sealed over it.

2. The biocompatible housing of claim 1, wherein the recess further comprises at least one biocompatible sealant covering the at least one feedthrough assembly.

3. The biocompatible housing of claim 1, wherein the hermetically sealed top cover further comprises gluing and/or welding.

4. The biocompatible housing of claim 1, wherein the at least one feedthrough assembly further comprises a sealant under the protective cap.

5. The biocompatible housing of claim 4, wherein the top cover further comprises a plurality of holes.

6. The biocompatible housing of claim 4, wherein the top cover further comprises a plurality of reinforcement ribs.

7. The biocompatible housing of claim 4, wherein the at least one feedthrough further comprises multiple feedthrough assemblies, and the at least one wire exit port further comprises multiple wire exit ports.

8. The biocompatible housing of claim 2 further comprising a second biocompatible sealant covering the biocompatible sealant.

9. A method to form a protective cap over a feedthrough assembly of an implantable medical device, the method comprising the steps of:
   forming a top having a thickness ranging from about 0.2 mm to about 2.0 mm;
   forming a gap under the top ranging from about 0.25 mm to about 25 mm;
   forming a mounting ridge on the top to match a shape and size of a receiving surface base on the feedthrough assembly;
   cleaning the receiving surface and the mounting ridge with a solvent and/or air and/or plasma;
   connecting a bundle of feedthrough wires to a plurality of feedthrough pads;
   welding or gluing the mounting ridge to the receiving surface base;
   passing the wire bundle through an exit port of the top; and
   injecting a sealant(s) into the exit port.

10. A method of manufacturing an implantable medical device, the medical device having a feedthrough subassembly comprising the at least one feedthrough assembly of claim 1 and additional components, comprising the steps of:
   a) Obtaining a composite assembly, the composite assembly being the feedthrough subassembly; and
   b) integrating the feedthrough subassembly with the additional components, thereby forming the implantable medical device.

* * * * *